United States Patent [19]

Jarvik

[11] Patent Number: 5,603,337
[45] Date of Patent: Feb. 18, 1997

[54] TWO-STAGE CARDIOMYOPLASTY

[76] Inventor: Robert Jarvik, 124 W. 60 St., New York, N.Y. 10023

[21] Appl. No.: 350,272

[22] Filed: Dec. 5, 1994

[51] Int. Cl.⁶ .................................................. A61B 19/00
[52] U.S. Cl. .......................................... 128/898; 600/16
[58] Field of Search ................ 128/897–99; 600/16–18, 600/37; 623/3; 607/119, 2, 3; 601/153

[56] References Cited

U.S. PATENT DOCUMENTS

| | | | |
|---|---|---|---|
| 4,403,604 | 9/1983 | Wilkinson et al. | 600/37 |
| 5,256,132 | 10/1993 | Snyders | 600/37 |
| 5,480,436 | 1/1996 | Bakker et al. | 600/37 |

FOREIGN PATENT DOCUMENTS

| | | | |
|---|---|---|---|
| 0014861 | 1/1985 | Japan | 128/897 |
| 2006738 | 4/1992 | WIPO | 600/110 |

OTHER PUBLICATIONS

Davol Rubber Co., "Complete Evisceration of Small Bowel . . ." 1959.
Chiu, "Using Skeletal Muscle for Cardiac Assistance", *Scientific American Science & Medicine*, Nov./Dec. 1994.

*Primary Examiner*—Angela D. Sykes
*Assistant Examiner*—John P. Lacyk

[57] ABSTRACT

Heart failure may be treated by grafting a skeletal muscle around the heart in a procedure called cardiomyoplasty. The muscle graft is stimulated to contract in synchrony with the heart by a burst stimulator, and the procedure has been shown to have some benefits. However, the operative and early mortality is high (nearly 50% 2-year mortality). The present invention recognizes a fundamental limitation to the effectiveness of cardiomyoplasty when applied to a markedly enlarged heart, due to the length tension characteristics of muscle. A two-stage procedure is provided, whereby the enlarged heart is first treated with a mechanical cardiac assist pump to reduce it to near normal size. Then a second surgical procedure, in which an optimal length of muscle is grafted to the heart, is performed about 4–6 weeks later. The muscle to be grafted may be preconditioned by electrical stimulation within a pouch designed to prevent tissue adhesions, during the time that the heart is being reduced in size with mechanical assistance.

5 Claims, 3 Drawing Sheets

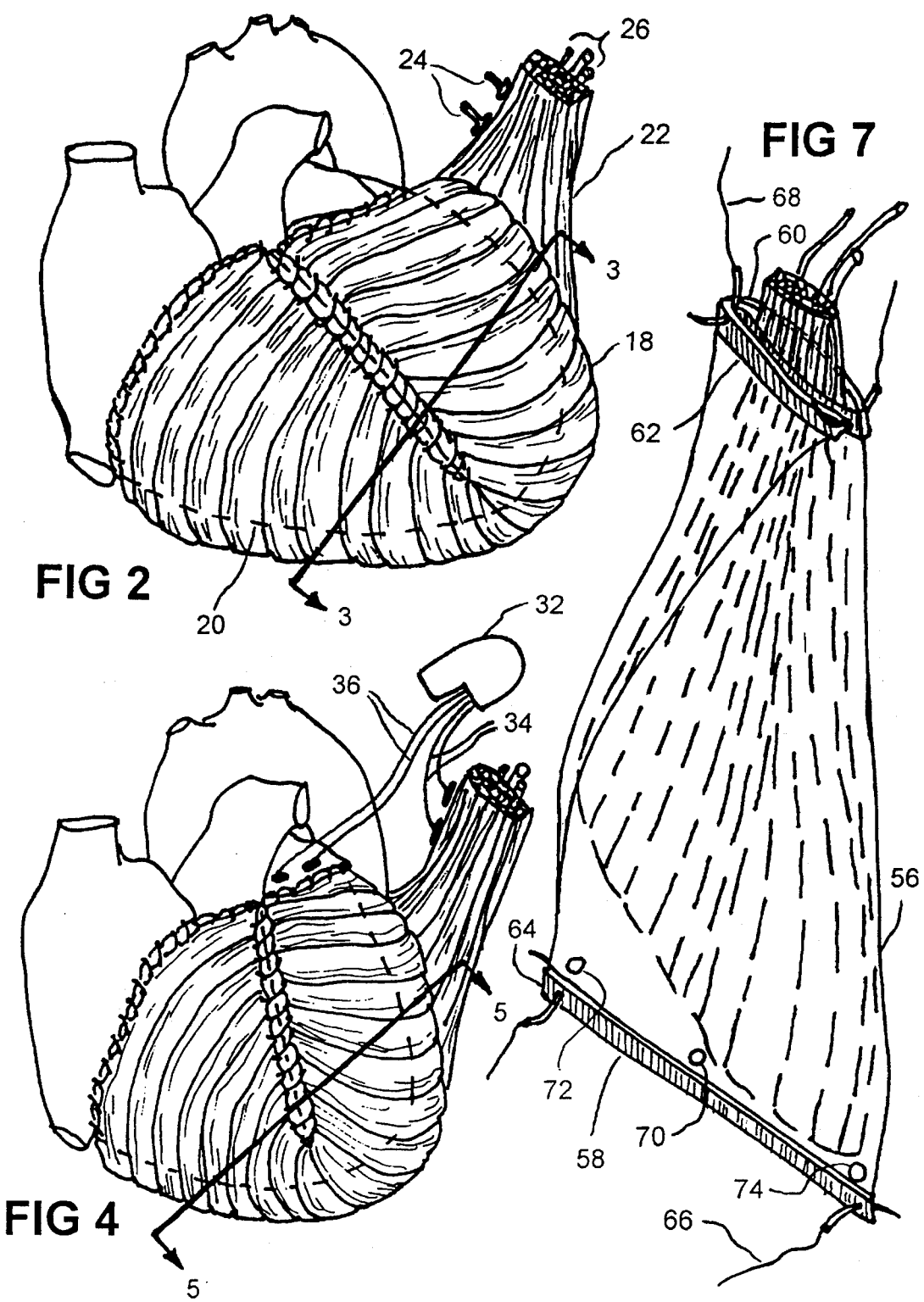

TWO-STAGE CARDIOMYOPLASTY

BACKGROUND OF THE INVENTION

Cardiomyoplasty is a method of treating congestive heart failure by wrapping the natural heart with skeletal muscle and stimulating that muscle with a "pacemaker"-like device. Use of burst-type stimulators transforms the skeletal muscle cells from slow-twitch, Type I fibers to fast-twitch, Type II fibers more like cardiac muscle cells and makes the transformed fibers capable of sustaining repeated rhythmic contraction with much less fatigue than normal skeletal muscle. However, it takes more than a month for the burst-stimulated skeletal muscle cells to become conditioned and transformed sufficiently to sustain repeated contraction without fatigue. During this time, about 10% of the patients die following myoplasty surgery, because their hearts are too weak to pump sufficiently. Additionally, although cardiomyoplasty has been found to improve cardiac functional class somewhat in surviving patients, mortality with the procedure is very high. About 10% of patients die at surgery, another 10% shortly following surgery, and in total about one third of patients die within a year of surgery. A recent study of long-term survival found 46% mortality after only 2 years.

The present invention provides a method by which the short-term mortality can be greatly reduced, the effectiveness of the skeletal muscle used to aid the heart can be increased, and both long-term survival and hemodynamic function can be improved significantly.

OBJECTS OF THE INVENTION

It is an object of the present invention to improve the effectiveness of cardiomyoplasty and reduce the operative and postoperative mortality.

It is another object of the present invention to provide a two-stage surgical procedure utilizing a cardiac assist device to reduce the size of the enlarged diseased heart prior to cardiomyopathy and thus permit wrapping of the heart with the optimal length of graft muscle tissue.

It is a further object of the present invention to provide a two-stage procedure in which the graft muscle is transformed to Type II muscle while the natural heart is assisted mechanically to reduce its size.

It is a still further object of the invention to provide a pouch in which the graft muscle can be maintained to prevent formation of adhesions between it and adjacent tissue while it is undergoing transformation by electrical stimulation or by other means.

THE DRAWINGS

FIG. 2 is a drawing of an enlarged dilated heart following a cardiomyoplasty procedure showing a latissimus dorsi muscle wrap.

FIG. 4 is a drawing of a normal-sized heart following a cardiomyoplasty procedure showing a latissimus dorsi muscle wrap.

Figure 1:
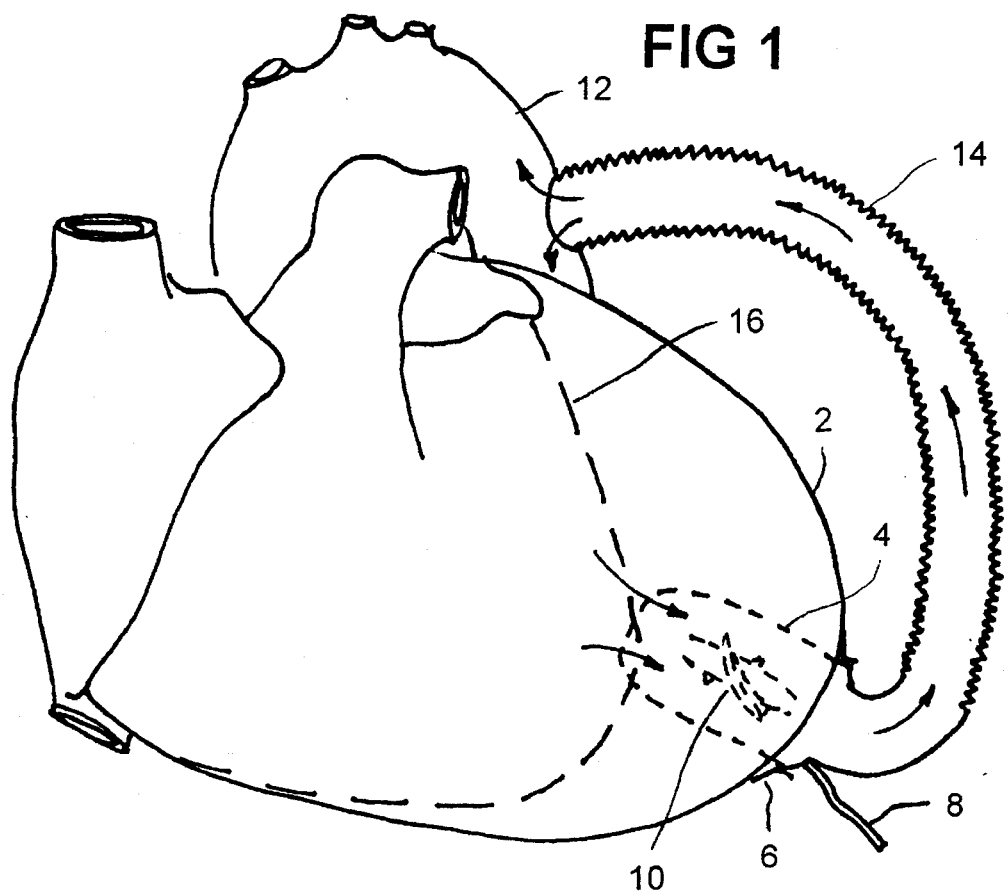
FIG. 1 is a line drawing of a enlarged dilated heart in which an intraventricular cardiac assist device has been implanted, also indicating the outline of the normal size of the ventricles.

FIGS. 6 A–G are a series of drawings representing sectional views of skeletal muscle in the relaxed and contracted states either laid out flat or wrapped around enlarged or normal sized hearts.

FIG. 7 is an illustration of a muscle conditioning pouch containing a dissected latissimus dorsi muscle, and folded over at one end.

GENERAL DESCRIPTION OF THE INVENTION

The invention comprises the method of performing cardiomyoplasty in a two-stage operation combined with mechanical circulatory support, and is based on the recognition of a mechanism whereby the effectiveness of cardiomyoplasty can be improved. When heart failure becomes severe, the heart enlarges and dilates. The cardiac muscle fibers become stretched and contract inefficiently. It is well known that reversing the enlargement of the heart improves its performance and this has long been a clinical goal of heart failure treatment. However, in patients with severe end-stage heart failure, medical treatment including drugs and salt restriction is no longer effective in reducing the size of the heart.

Dilated congestive heart failure patients are exactly the patients that most commonly undergo cardiomyoplasty. In this situation, when the latissimus dorsi muscle is wrapped around the dilated heart, a relatively long length of the latissimus dorsi muscle is required to surround the ventricle. The contraction of the muscle when it is rhythmically stimulated improves the cardiac hemodynamics, and reduces the load on the natural heart muscle fibers. As a result of this, the dilatation of the natural heart begins to be reversed. As the natural heart shrinks back towards normal size this causes the grafted muscle to be too long and therefore ineffective when it contracts. The muscle wrap becomes loose around the natural heart rather than having a snug fit. Thus the degree of improvement is self limiting. The more the natural heart tends to improve, the less effective the muscle wrap becomes, and so the muscle wrap is mechanically incapable of providing improvement beyond a certain point. What is required is to first shrink the dilated heart down to near normal size, and then attach the muscle wrap so that a shorter length of muscle graft is used. In this way the wrapped muscle, such as latissimus dorsi, is most effective at supporting the natural heart function, and its geometry remains optimal.

Mechanical circulatory support, particularly with long-term Left Heart Assist Devices, has become a common technique of sustaining the lives of patients awaiting heart transplant. Many patients have had significant dilatation of the heart at the time the LVADs were implanted. After several weeks of pumping, this cardiac dilatation is usually reversed, with the heart returning to more normal size.

Two conditions must be met to optimize the effectiveness of cardiomyoplasty. First, the heart must be reduced to near normal size at the time the muscle wrap procedure is done, so that the proper length of muscle can be used, and second, the muscle should already be conditioned and transformed to Type II fibers to reduce early postoperative mortality due to muscle fatigue.

In the method of the present invention, a cardiac assist device is first applied to the patient and utilized for about six weeks to completely unload the patient's natural heart and shrink it to near normal size. The muscle which is to be used for the cardiomyoplasty wrap can be simultaneously stimulated with a burst stimulator, or otherwise treated pharmacologically such as with local injection of hormones such as triiodothyronine to transform the muscle fibers to Type II and render the muscle resistant to fatigue. The muscle may be dissected free from its natural anatomic location and moved into the chest cavity at the time the cardiac assist device is implanted. If this is done without shielding the surface of the muscle from contact with other tissues, adhesions will form between the muscle and these tissues. Therefore, the invention provides a polymer pouch made of a material which is resistant to the formation of adhesions, into which the muscle is placed to prevent the formation of adhesions and thereby facilitate the second surgery.

SPECIFIC DESCRIPTION OF THE INVENTION

Referring to FIG. 1, the outline of the enlarged heart is indicated at 2. A ventricular assist device 4 is inserted into the left ventricle, retained at the apex by a sewing cuff 6 and powered electrically via a power cable 8. In this embodiment, the assist device contains an axial flow pump 10 which pumps the blood from the left ventricle 2 to the aorta 12 via a vascular graft 14. After a few weeks of assist pumping in which the pump fully unloads the left ventricle, the heart shrinks down to near normal size as indicated by the dashed outline 16.

Figure 3:
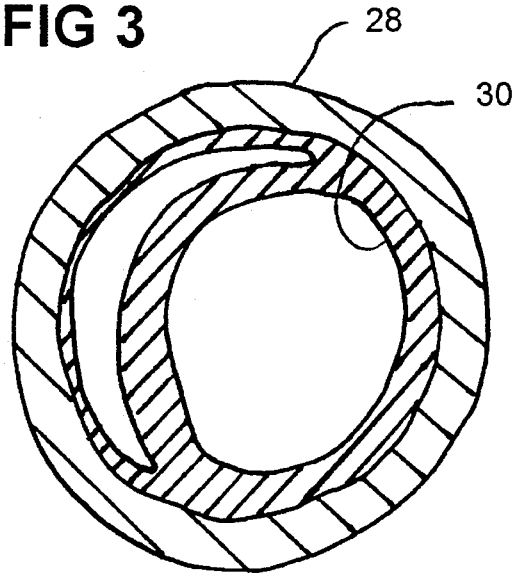
FIG. 3 is a sectional view through the heart of FIG. 2 along line 3—3.

FIG. 2 shows an enlarged heart that has been wrapped with the left latissimus dorsi muscle 18 in a standard cardiomyoplasty procedure without first being assisted mechanically to reduce its size to near normal. The outline of the heart muscle is indicated by a dashed line at 20 illustrating that a sheetlike covering of latissimus dorsi muscle surrounds the heart. A pedicle of the muscle 22 is stimulated by electrodes 24. The pedicle permits nerves, arteries, and veins 26 to remain connected to the muscle when it is moved from its normal position to its location around the heart. FIG. 3 shows the muscle wrap 28 around the natural heart 30. The natural heart is dilated and has a large circumference requiring a long length of latissimus dorsi to surround it.

Figure 5:
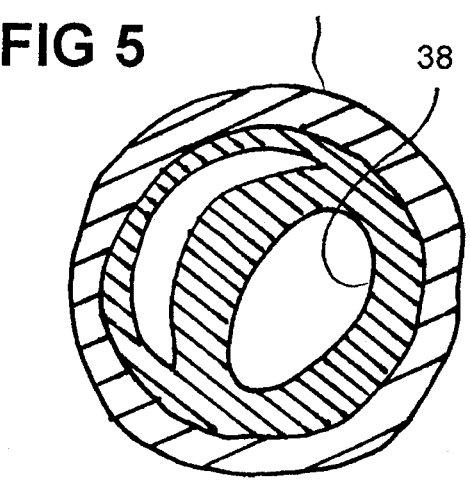
FIG. 5 is a sectional view through the heart of FIG. 4 along line 5—5.
Figure 6A:
Figure 6B:
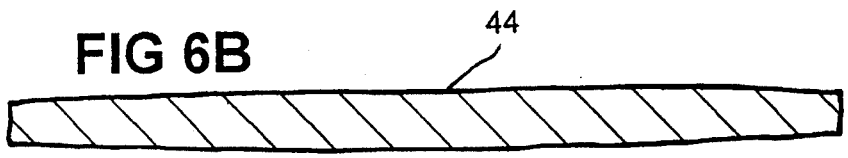
Figure 6C:
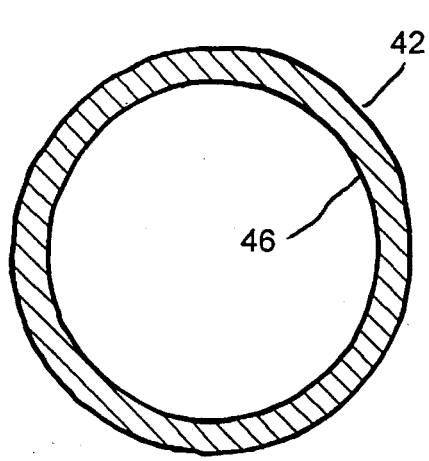
Figure 6D:
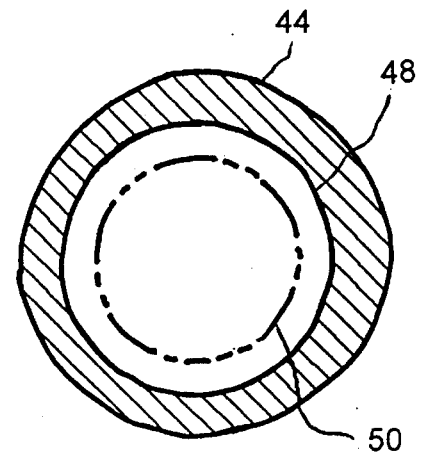
Figure 6E:
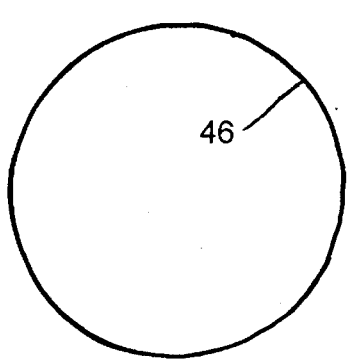
Figure 6F:
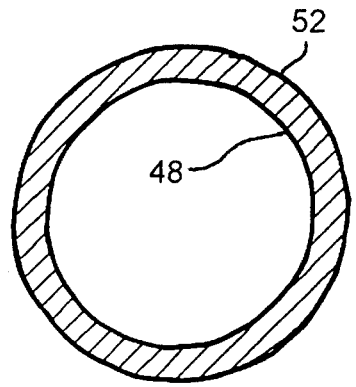
Figure 6G:
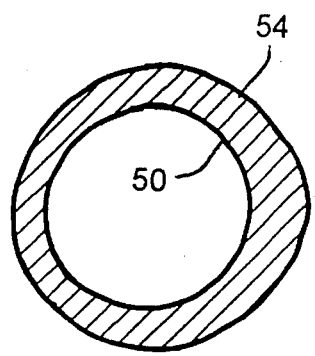

FIG. 4 shows a heart which has been reduced in size to near normal by the use of a ventricular assist device, after the cardiomyoplasty procedure. The burst stimulator 32 delivers the stimulating current to the muscle graft via stimulating electrodes 34 in synchrony with the natural heart contraction as determined by sensing electrodes 36. As illustrated in section in FIG. 5, the circumference of the natural heart 38 is much reduced compared to its previous enlarged condition, which would have been like the dilated heart shown in FIG. 3. Thus, a much shorter circumferential length of latissimus dorsi muscle 40 is required to surround it. This is further illustrated in FIG. 6. FIG. 6A represents a sectional view of a length of latissimus dorsi muscle 42 in the non-contracting state stretched beyond its resting length sufficiently to wrap around the circumference of a dilated heart and take the form illustrated in FIG. 6C. This represents myoplasty as performed in the old way (without first using a cardiac assist device to shrink the heart) as shown in FIG. 3. FIG. 6C represents the circumference of the wrapped muscle when it is not stimulated and the heart is at the end diastole filled with blood to its greatest extent. FIG. 6B represents the same muscle as FIG. 6A but in the stimulated and contracted state 44 close to its rest length. It is shorter and thicker and cannot shorten much further. Muscle must be stretched beyond its rest length to exert force upon contraction. There is an optimal degree of stretch, corresponding to a sarcomere length of about 2 microns, at which the muscle develops the most tension. However, if it shortens much further, from a sarcomere length of about 1.67 microns to 1.27 microns the tension it can develop rapidly decreases from about 80% of maximum at 1.67 microns to zero at 1.27 microns. In the myoplasty procedure, the muscle cannot be stretched much when it is sewn around the heart because it exerts passive elastic force even when not contracting, and this force would be too high to permit the heart to fill with blood at normal filling pressures. Thus, when it is stimulated, it contracts to near its rest position but cannot shorten further. Once the circumference of the natural heart, illustrated by the inside circumference of the muscle graft 46, is reduced to about the rest length of the muscle graft as shown in FIG. 6D at 48 the myoplasty is ineffective to apply muscular force to further reduce the circumference to the normal end-systolic circumference 50. This is exactly why the conventional myoplasty procedure performed on an enlarged heart is unable to shrink the heart to normal size. The myoplasty muscle graft can only apply force effectively when the natural heart is dilated, which is a condition in which the natural heart muscle fibers are most ineffective due to being overstretched. This explains the fundamental principle of the two-stage procedure of this invention and why it is so beneficial to reduce the natural heart to near normal size before the myoplasty graft is wrapped around it. FIG. 6F illustrates a shorter length of latissimus dorsi muscle 52 that is used to wrap the heart after it has been reduced to normal size. The circumference 48 is less than the circumference 46 which would have been required in the dilated enlarged heart. Therefore when the muscle graft is stimulated to contract it is able to shorten as shown in FIG. 6G 54, and the circumference of the heart it surrounds is the normal end systolic circumference 50. This permits the myoplasty graft to apply force effectively when the natural heart is at its normal size, which is also when the natural heart is at the proper muscle fiber length to be most effective. Thus, the combination of graft and heart muscle size and force capability is optimal.

FIG. 7 illustrates a muscle conditioning pouch in which the dissected muscle can be maintained for 4–6 weeks while the muscle is transformed to Type II fibers. Stimulating electrodes are first placed on the muscle pedicle and the muscle is then introduced into a polymer bag 56 having a closed end 58 and an open end 60. Each end is reinforced with a thickened reinforcement 62 and 64 strong enough to hold sutures 66 and 68 without tearing even under considerable strain on the sutures. The closed end of the bag is provided with drainage holes 70, 72, 74, to permit fluid to exit. The bag and reinforcements are fabricated of an adhesion-resistant polymer, such as smooth polyurethane or smooth silicone rubber. In use, the muscle is placed in the pouch with its pedicle containing the blood supply and nerves extending across the open end. The bag is folded over and sutured in this configuration to retain the muscle inside without placing pressure on the pedicle. The muscle in the pouch is then placed in a suitable position to remain during the period of time it undergoes conditioning, and the end reinforcements 62, 64 are utilized to suture it to appropriate tissues to prevent it from becoming folded or bunched up. After some weeks, when the natural heart has been reduced to near normal size due to the effect of the assist device, the pouch is cut away, and the myoplasty procedure is completed.

The information disclosed in the description of the present invention is intended to be representative of the principles that I have described. It will thus be seen that the objects of the invention set forth above and those made apparent from the preceding description are efficiently obtained and that certain changes may be made in the above articles and constructions without departing from the scope of the invention. It is intended that all matter contained in the above description or shown in the accompanying drawings shall be interpreted as illustrative but not in a limiting sense. It is also understood that the following claims are intended to cover all of the generic and specific features of the invention herein described and all statements of the scope of the invention which as a matter of language might be said to fall there between.

I claim:

1. The method of two-stage surgical treatment of dilated congestive heart failure comprised of:

a. First, in the initial stage of said treatment, performing a first operation in which a cardiac assist device including a mechanical circulatory assist pump is applied to the patient to hemodynamically support the patient's left ventricle and cause it to become reduced from its dilated, enlarged size to a generally normal size, and then, b. Second, in the subsequent stage of said treatment, after the patient's heart has become reduced in size as a result of said mechanical assist, performing a second operation in which a skeletal muscle graft is applied to the heart and stimulated electrically such that its contraction assists the function of the heart.

2. The method of claim 1 in which during the time between said first and second operations while the cardiac assist device is functioning to reduce the size of the patient's heart, the skeletal muscle which will be applied to support the heart during the subsequent stage of said treatment, is electrically stimulated to cause it to undergo conditioning.

3. The method of claim 1 in which said cardiac assist device is removed at the time of said second operation.

4. The method of claim 2 in which said skeletal muscle is prepared for translocation to the heart by dissection and placement within the chest cavity during said first operation.

5. The method of claim 4 in which said muscle is covered with polymer material at the time of said first surgery and thus prevented from adhering to structures within the chest cavity until the time of said second operation.

* * * * *